United States Patent [19]
Greaves et al.

[11] Patent Number: 5,928,668
[45] Date of Patent: Jul. 27, 1999

[54] METHOD FOR DRY BLEND COMPRESSION OF MEDICAMENTS

[75] Inventors: Frank C. Greaves, Wilmington; James Swarbrick, Hampstead; Martin W. Beasley, Wilmington, all of N.C.

[73] Assignee: Applied Analytical Industries, Inc., Wilmington, N.C.

[21] Appl. No.: 08/649,719

[22] PCT Filed: Dec. 20, 1994

[86] PCT No.: PCT/US94/14639

§ 371 Date: Aug. 1, 1996

§ 102(e) Date: Aug. 1, 1996

[87] PCT Pub. No.: WO95/17169

PCT Pub. Date: Jun. 29, 1995

[30] Foreign Application Priority Data

Dec. 21, 1993 [ZA] South Africa ............................ 93/9566

[51] Int. Cl.⁶ ..................................................... A61K 9/14
[52] U.S. Cl. ........................... 424/489; 424/464; 424/465
[58] Field of Search ..................................... 424/449, 489, 424/464, 465

[56] References Cited

U.S. PATENT DOCUMENTS 3,568,828  3/1971  Lerner ........................................ 206/42
4,544,554  10/1985 Pasquale ................................. 514/170
4,684,534  8/1987  Valentine ..................................... 424/3
5,275,822  1/1994  Valentine et al. ....................... 424/489
5,585,370  12/1996 Casper .................................... 424/449
5,595,759  1/1997  Wright et al. ........................... 424/464

FOREIGN PATENT DOCUMENTS 0 179 703  4/1986  European Pat. Off. .
0 371 466  6/1990  European Pat. Off. .
0 503 521  9/1992  European Pat. Off. .

*Primary Examiner*—Thurman K. Page
*Assistant Examiner*—W. Benston
*Attorney, Agent, or Firm*—Finnegan, Henderson, Farabow, Garrett & Dunner, L.L.P.

[57] ABSTRACT

Disclosed is a method of dry blend compression of potent drugs with low solubility, such as steroidal medicaments using directly compressible agglomerated excipients that are not a conventional or spray dried polyalcohol or lactose. The agglomerated excipients include mannitol, maltodextrin or corn syrup solids, which hold the medicament(s) in the crevices of the agglomerates. Also disclosed are the critical ratios of the agglomerated excipients to steroidal agent, specifically estradiol, that is distributed uniformly throughout the dry blend and then compressed into tablets.

7 Claims, No Drawings

METHOD FOR DRY BLEND COMPRESSION OF MEDICAMENTS

TECHNICAL FIELD

This invention relates to a method of dry blend compression of insoluble potent drug substances using a directly compressible, agglomerated excipient that is not a conventional spray dried polyalcohol or lactose.

BACKGROUND ART

Inadequate distribution of low-dose potent drugs is a constant threat to the uniform potency of tablets and capsules containing such drugs.

The greatest potential for drug-diluent segregation in a tablet system occurs with powder or particulate mixtures intended for direct compression or wet granulation in which the drug migration occurs (Dale E. Fonner et. al., Pharmaceutical Dosage Forms: Tablets, Volume 2, pp. 253.). European Patent Application 92103963.2, AKZO N. V. p. 6 describes the inadequate homogeneity encountered with compositions containing hydrous lactose DT (U.S. Pat. No. 4,544,554 etc. issued to Samuel A. Pasquale). The migration of a low-dose potent drug disrupts the distribution throughout the mix, giving rise to inconsistency in the content uniformity of the dosage form.

U.S. Pat. No. 3,568,828 issued to Leonard Joseph Lerner describes wet processes using potent drug substances such as estrogens with organic solvents such as chloroform. Such processes are now regarded as environmentally unsafe and can incur considerable manufacturing expenses, in that appropriate solvent scrubbing and/or explosion proof equipment must be acquired at substantial capital expenditure.

Estradiol and a number of other low-dose potent drugs precipitate in a variety of polymorphs and/or crystal habits. The changes in the crystal structure on drying can affect the bioavailability of the drug. It is well known in the literature that the micronized form is more bioavailable than larger drug particle size. This invention offers an important alternative to wet granulation, thus eliminating recrystallization and the issue of polymorphism and bioavailability. It also offers the choice of dry mixing or direct compression with materials other than the conventional spray dried polyalcohols or lactoses.

DISCLOSURE THE INVENTION

The following describes the use of low dose medicinal agents such as micronized steroidal medicinal agents; estradiol, equilin, estrone, spironolactone, and non-micronized materials; such as, estropipate, conjugated estrogens, esterified estrogens, progestins or other medicinal agents having the structure which includes the cyclopentanoperhydrophenanthrene ring system which agents are formulated by a drug pharmaceutical preparation. The dry preparation makes use of excipients that have been prepared by agglomeration methods other than by spray drying. Such excipients include granular mannitol, agglomerated maltodextrin, corn syrup solids and mixtures of these agents with added conventional direct compression excipients.

The active ingredients comprise any medicament which has a low effective dose such as those below 10 mg per dosage unit. Most useful are those medicaments having a steroidal nucleus, the cyclopentanoperhydrophenanthrene ring system, in their chemical structures such as the estrogens or progestins.

Examples of the former are ethinylestradiol, estrone, mestranol, 17-alpha-ethinyl estradiol-3-methylether, esterified estrogens, and, especially estradiol, conjugated estrogens, methyl testosterone. The dosage amounts and indications of these and other active ingredients are those described in the literature such as the Physician's Desk Reference.

The progestins are 3-ketodesogestrel, desogestrel, levodesogestrel, norgestrel, gestodene, norethindrone, norethindrone acetate.

Other medications known to the art which are used in low doses are spironolactone, digoxin, glipizide, estazolam, clorazepate dipotassium, albuterol sulfate, clonidine HCL, alprazolam.

The agglomerated excipients used in this method are those listed above. These are differentiated from those used in the AKZO method of reference in not having the AKZO prescribed affinity-demixing range of properties of active ingredient to dry excipient. The latter property gives the method of this invention a commercial advantage in manufacturing procedure.

Studies comparing the properties of the AKZO preferred excipient (spray dried lactose) with applicant's lead species (agglomerated mannitol) demonstrated that the former retained 2 to 3 times the quantity of estradiol on its surface than did the claimed ingredient. The tablet of this invention, however, gave good drug distribution figures despite not having the high affinity AKZO states to be necessary.

Also, photomicrographs of the samples demonstrated that the AKZO mix had drug uniformly attached to all the surfaces of the excipient. In contrast, the mix of this invention had drug located in crevices of the agglomerate. This indicates a different mechanism of attachment.

The method of this invention, therefore, comprises mixing one or more low-dose medicaments with the agglomerated excipient, usually in a ratio of from about 1:40 to 1:100, medicament to excipient. Other excipients, disintegrating agents or lubricants are optionally added. After dry mixing, the mix is compressed into tablets.

The following examples illustrate the method of this invention in more detail.

EXAMPLE I

| ESTRADIOL 2 mg TABLETS | | | |
|---|---|---|---|
| Materials | A (%) | B (%) | C (%) |
| Microcrystalline Cellulose (Avicel PHI 02) | 45.89 | 23.20 | — |
| Starch 1500 | — | 20.00 | 20.00 |
| Dibasic Calcium Phosphate (Cal-Star) | — | — | 23.20 |
| Agglomerated Mannitol | 47.39 | 50.08 | 50.08 |
| Croscarmellose Sodium (Ac-Di-Sol) | 5.00 | 5.00 | 5.00 |
| Magnesium Stearate | 0.50 | 0.50 | 0.50 |
| Estradiol | 1.22 | 1.22 | 1.22 |

1. Screen estradiol and mannitol together through a #20 mesh screen into a slant-cone high speed mixer.
2. Screen Avicel PH 102 and Ac-Di-Sol through the screen and force any remaining estradiol through as well.
3. Blend for fourteen (14) minutes with the agitator bar off, two (2) minutes with the agitator bar on, and blend fourteen (14) minutes with the agitator bar off (total of thirty (30) minutes).
4. Add the magnesium stearate and blend for three (3) minutes with the agitator bar off.
5. Compress into tablets on a high speed tablet press. Tablet weight of 1 64±3%.

Other Illustrations are:
1. Using the process of example 1 with agglomerated maltodextrin blended with estradiol and a progestin.
2. Using the process of example 1 with a combination of agglomerated mannitol and maltodextrin blended with an estrogen or a progestin or a combination of estrogen and progestin.
3. Using the process of example 1 with a combination of agglomerated mannitol and maltodextrin blended with conjugated estrogens alone or in combination with a progestin.

What is claimed is:

1. A pharmaceutical composition comprising one or more low dosage medicaments and an agglomerated excipient in a ratio from about 1:40 to about 1:100 of medicament to excipient; wherein the agglomerated excipient is selected from the group consisting of mannitol, maltodextrin, corn syrup solid, and mixtures thereof and, optionally, one or more excipient, disintegrating agent, or lubricant.

2. The composition of claim 1 wherein said medicament is an estrogen and, optionally, a progestin.

3. The composition of claim 2 wherein said estrogen is estradiol.

4. The composition of claim 2 wherein said estrogen is a conjugated estrogen.

5. The composition of claim 4 wherein said progestin is medroxyprogesterone acetate.

6. The composition of any one of claims 2 or 1 wherein the excipient is selected from the group consisting of mannitol, maltodextrin, or a combination thereof.

7. The composition of any one of claims 2 or 1 wherein said composition is in the form of a tablet.

* * * * *

UNITED STATES PATENT AND TRADEMARK OFFICE
CERTIFICATE OF CORRECTION

PATENT NO.: 5,928,668

DATED: July 27, 1999

INVENTOR(S): Frank C. Greaves, James Swarbrick, Martin W. Beasley

It is certified that an error appears in the above-identified patent and that said Letters Patent is hereby corrected as shown below:

In claim 6, column 4, line 11, change "2 or 1" to --2 to 5 or 1--.

In claim 7, column 4, line 14, change "2 or 1" to --2 to 5 or 1--.

Signed and Sealed this

Seventh Day of December, 1999

Attest:

Q. TODD DICKINSON

Attesting Officer

Acting Commissioner of Patents and Trademarks